United States Patent [19]

Okada et al.

[11] Patent Number: 5,463,009
[45] Date of Patent: Oct. 31, 1995

[54] FLUORINE-MODIFIED SILICONE, PROCESS FOR PREPARING THE SAME, AND COSMETICS CONTAINING THE SAME

[75] Inventors: Jouji Okada, Tochigi; Akira Kawamata, Wakayama; Tadayuki Tokunaga, Chiba; Makoto Torizuka, Kanagawa; Masahiko Asahi, Tokyo, all of Japan

[73] Assignee: Kao Corporation, Tokyo, Japan

[21] Appl. No.: 354,756

[22] Filed: Dec. 8, 1994

[30] Foreign Application Priority Data

Dec. 9, 1993 [JP] Japan .................................. 5-309133

[51] Int. Cl.$^6$ .......................................... C08G 77/08
[52] U.S. Cl. ................... 528/15; 528/26; 528/42; 556/488; 556/479; 514/844; 514/845; 514/846
[58] Field of Search ................... 528/42, 15, 26; 556/488, 479

[56] References Cited

U.S. PATENT DOCUMENTS 3,833,632  9/1974  Meiller et al. ........................ 528/42
4,992,521  2/1991  Saito et al. ............................ 528/42

Primary Examiner—Melvyn I. Marquis
Attorney, Agent, or Firm—Oblon, Spivak, McClelland, Maier, & Neustadt

[57] ABSTRACT

A fluorine-modified silicon compound having a polymerization degree of from 1 to 400 and containing at least one siloxane unit represented by formula (1):

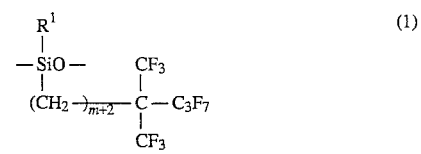

wherein $R^1$ represents an aliphatic straight-chain or branched hydrocarbon group having 1 to 20 carbon atoms or an alicyclic hydrocarbon group having 5 to 10 carbon atoms or an aromatic hydrocarbon compound having 6 to 10 carbon atoms; and m represents 0 or an integer of from 1 to 10; a process for preparing the same; and a cosmetic containing the same are disclosed. The fluorine-modified silicone derivative exhibits high water- and oil-repellency to provide cosmetics which wear long and have a good feel on use.

4 Claims, No Drawings

FLUORINE-MODIFIED SILICONE, PROCESS FOR PREPARING THE SAME, AND COSMETICS CONTAINING THE SAME

FIELD OF THE INVENTION

This invention relates to a fluorine-modified silicone, a process for preparing the same, and cosmetics containing the same. More particularly, it relates to a novel fluorine-modified silicone having excellent water- and oil-repellency, a process for preparing the same, and cosmetics containing the same which wear long when applied to the skin and have a good feel on use.

BACKGROUND OF THE INVENTION

Various types of water-repellent cosmetics are used for protecting the skin from water or sweat or for preventing makeup from getting disordered by water or sweat. For example, cosmetics for foundation, such as creams and lotions, and cosmetics for make-up usually contain silicone oil or silicone resin as a water-repellent component. The silicone oil or silicone resin is effective for water-repellency to some extent but does not have sufficient oil-repellency. Therefore, cosmetics containing these ingredients still tend to get disordered on the skin due to sebum.

Hence, attempts have been made in various fields to develop a compound which repels both water and oil. For example, JP-A-2-295912 (the term "JP-A" as used herein means an "unexamined published Japanese patent application") discloses that cosmetics containing fluorine-modified silicone compounds, such as trifluoropropylsilicone, exhibits excellent resistance to both water and sebum.

A water- and oil-repellent base to be used in cosmetics should satisfy all the requirements: (a) to have sufficient repellency against sweat and sebum, (b) to have excellent emulsion stability, (c) to withstand mechanical contact (for example, when pressed with a handkerchief or a tissue), and (d) to have a controlled viscosity to give a good feel on application.

However, the known fluorine-modified silicone compounds do not sufficiently fulfill these requirements. That is, they have poor emulsion stability due to poor compatibility with general cosmetic bases, they easily come away on contact with a handkerchief, a tissue, etc. due to poor affinity to the skin, and they have poor spreadability on application to the skin because of high viscosity.

It has therefore been demanded to develop a compound having excellent water- and oil-repellency which is stable when incorporated into cosmetics, causes no disorder of makeup while on the skin, and gives a satisfactory feel on use.

SUMMARY OF THE INVENTION

As a result of extensive investigations, the present inventors have found that a fluorine-modified silicone derivative having a specific branched perfluoroalkyl group exhibits not only excellent water- and oil-repellency but has good affinity to the skin and satisfactory compatibility with other cosmetic ingredients. The present invention has been completed based on this finding.

The present invention relates to a fluorine-modified silicon compound having a polymerization degree of from 1 to 400 and containing at least one siloxane unit represented by formula (1):

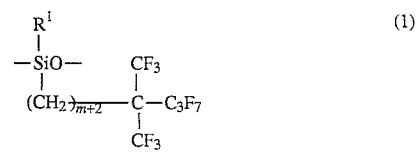

wherein $R^1$ represents an aliphatic straight-chain or branched hydrocarbon group having 1 to 20 carbon atoms or an alicyclic hydrocarbon group having 5 to 10 carbon atoms or an aromatic hydrocarbon group having 6 to 10 carbon atoms; and m represents 0 or an integer of from 1 to 10.

The present invention further relates to a process for preparing the above-mentioned fluorine-modified silicone derivative.

The present invention furthermore relates to a cosmetic containing the above-mentioned fluorine-modified silicone derivative.

DETAILED DESCRIPTION OF THE INVENTION

The fluorine-modified silicone derivative according to the present invention (hereinafter referred to as silicone derivative (A)) has a polymerization degree of 1 to 400, that is, comprises 1 to 400 siloxane units, at least one of which is a fluorine-modified siloxane unit represented by formula (1) (hereinafter referred to unit (1)). Silicone derivative (A) preferably comprises 1 to 200 units of (1) and from 0 to 200 siloxane units represented by formula (2) (hereinafter referred to as unit (2)):

wherein $R^2$ and $R^3$, which may be the same or different, each represent an aliphatic straight-chain or branched hydrocarbon group having 1 to 20 carbon atoms or an alicyclic hydrocarbon group having 5 to 10 carbon atoms or an aromatic hydrocarbon group having 6 to 10 carbon atoms or an aromatic hydrocarbon group having 6 to 10 carbon atoms.

In silicone derivatives (A), the hydrocarbon groups represented by $R^1$, $R^2$ or $R^3$ include a straight-chain alkyl group, such as methyl, ethyl, propyl, butyl, pentyl, hexyl, heptyl, octyl, nonyl and decyl; a branched alkyl group, such as isopropyl, sec-butyl, tert-butyl, neopentyl, 1-ethylpropyl and 2-ethylhexyl; a cycloalkyl group, such as cyclopentyl and cyclohexyl; and an aromatic hydrocarbon group, such as phenyl and naphthyl.

The number (p) of units (1) in silicone derivative (A) is preferably from 1 to 200, more preferably from 1 to 50; and the number (q) of units (2) is preferably from 0 to 200, more preferably from 0 to 50, still more preferably from 2 to 50. The ratio of units (1) to units (2) in number, p/q, preferably falls within a range of from 4/1 to 1/4. Of silicone derivatives (A), those having unit(s) (1) in the chain thereof, i.e., side chain type modified silicone derivatives, are preferred.

Preferred examples of the side chain type modified silicone derivative include those represented by formula (A') (hereinafter referred to as silicone derivative (A')):

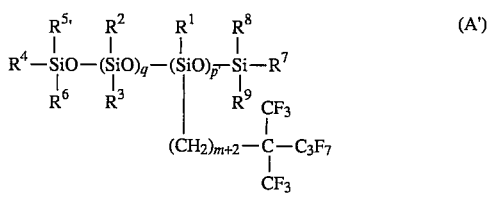

wherein p' represents 0 or an integer of 1 to 200; when p' is an integer of 1 to 200, $R^4$, $R^5$, $R^6$, $R^7$, $R^8$ and $R^9$, which may the same or different, each represents an aliphatic straight-chain or branched hydrocarbon group having 1 to 20 carbon atoms or an alicyclic or aromatic hydrocarbon group having 5 to 10 carbon atoms; when p' is 0, at least one of $R^4$, $R^5$, $R^6$, $R^7$, $R^8$, and $R^9$ represents a group $-(CH_2)_{m+2}-C(CF_3)_2(C_3F_7)$, and the others independently represent an aliphatic straight-chain or branched hydrocarbon group having 1 to 20 carbon atoms or an alicyclic or aromatic hydrocarbon group having 5 to 10 carbon atoms; and $R^1$, $R^2$, $R^3$, m, and q are as defined above.

Examples of the group represented by $R^4$ to $R^9$ include those cited above in connection with the group represented by $R^1$ to $R^3$.

Among silicone derivatives (A'), those represented by formulae (A'-1), (A'-2), and (A'-3) shown below are more preferred, with those represented by formula (A'-3) being particularly preferred.

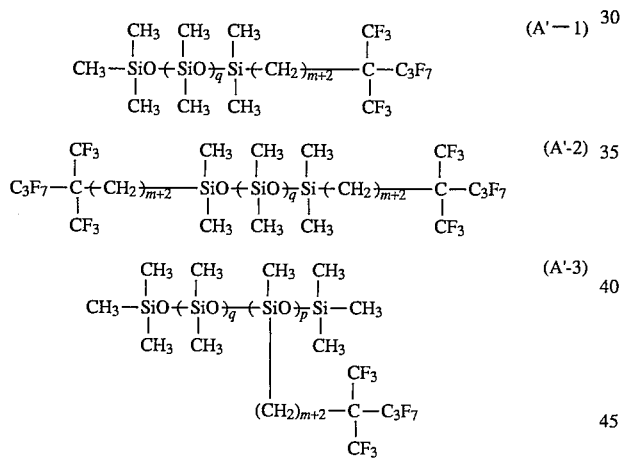

wherein m, p, and q are as defined above.

Silicone derivative (A) according to the present invention can be prepared by reacting a silicone derivative comprising a siloxane unit represented by formula (3):

wherein $R^1$ is as defined above, and having a degree of polymerization of from 1 to 400 (hereinafter referred to as silicone derivative (B)) with a perfluoroalkyl compound represented by formula (4):

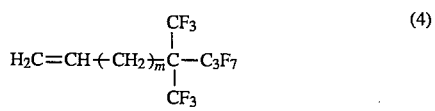

wherein m represents 0 or an integer of from 1 to 10.

Silicone derivative (B) is not particularly limited in molecular structure, etc. as long as it contains at least one siloxane unit of formula (3), and various known siloxane compounds may be used. Examples of suitable silicone derivatives (B) include one-terminal type methylhydrogenpolysiloxanes, such as pentamethyldisiloxane and tridecamethylhexasiloxane; two-terminal type methylhydrogenpolysiloxanes, such as tetramethyldisiloxane, hexamethyltrisiloxane, octamethyltetrasiloxane, and dodecamethylhexasiloxane; and commercially available methylhydrogenpolysiloxanes, such as TSF 484 and TSF 483, produced by Toshiba Silicone Co., Ltd., and KF 99, produced by Shin-Etsu Chemical Co., Ltd.

The perfluoroalkyl compound of formula (4) can be prepared by a known process, for example, according to the process described in W. Dmowski and Wozniacki, *J. Fluorine Chem.*, Vol. 36, p. 385 (1987) as follows.

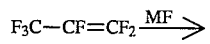

(5)

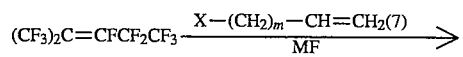

(6)

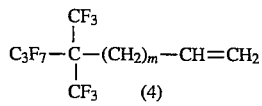

(4)

wherein M represents an alkali metal; X represents a halogen atom, e.g., Cl, Br or I; and m is as defined above.

That is, compound (4) is obtained by reacting compound (6), which is the dimer of hexafluoropropene (5), with halogenated alkane (7). For reactivity and economy, halogenated alkane (7) in which m is from 0 to 8 and X is Br or I, such as a vinyl halide, an allyl halide, a butene halide, a hexene halide, an octene halide, a decene halide, or a dodecene halide, is preferred. Compound (7) is used in an amount of at least 1 molar equivalent, preferably from 1.0 to 1.5 molar equivalents, to compound (6). The reaction is carried out at a temperature of from 0° to 200° C., preferably of from 10° to 100° C., while stirring with or without a solvent.

The reaction between compound (4) and silicone derivative (B) is carried out in the presence of a catalyst generally employed for hydrosilylation, such as a free radical initiator and a metal complex compound of ruthenium, rhodium, palladium, osmium, iridium, platinum, etc., either as such or as supported on silica gel or alumina. Preferred of them are chloroplatinic acid and a Speier reagent (an isopropyl alcohol solution of chloroplatinic acid). The catalyst is used in an amount enough to accelerate the reaction between silicone derivative (B) and compound (4), preferably of from $10^{-6}$ to $10^{-1}$ mols per mol of compound (4).

While not limiting, the reaction may be performed in a solvent. The solvent is selected appropriately from those inert to the reaction, such as aliphatic or alicyclic hydrocarbons, such as pentane, hexane and cyclohexane; aromatic hydrocarbons, such as benzene, toluene and xylene; ethers, such as diethyl ether and diisopropyl ether; and alcohols, such as methanol, ethanol, isopropyl alcohol, and butanol.

The hydrosilylation reaction proceeds at a temperature ranging from 0° to 200° C. Taking the reaction rate and coloration of the product into consideration, the reaction is preferably performed at a temperature of from 40° to 150° C. for a period of from 0.5 to 24 hours.

Various properties of the resulting fluorine-modified silicone derivatives (A), such as viscosity, solubility, and emulsion stability, can be controlled by appropriately adjusting the kinds or amounts of silicone derivative (B) and compound (4).

Silicone derivatives (A) according to the present invention are excellent in water- and oil-repellency and their physical properties, such as viscosity, can be controlled according to the end use. Therefore, they are useful as an oil of cosmetics to provide cosmetics that wear long and have a good feel on use. The proportion of silicone derivative (A) in cosmetics is not particularly restricted and usually ranges from 0.001 to 90% by weight, preferably from 0.01 to 80% by weight, more preferably from 0.1 to 70% by weight, and still more preferably from 3 to 30% by weight.

If desired, the cosmetics containing silicone derivative (A) may further contain other oil components for common cosmetics. Other usable oil components include cyclic silicones, such as octamethylcyclotetrasiloxane, decamethylcyclopentasiloxane, and dodecamethylcyclohexasiloxane; nonvolatile silicones, such as methylpolysiloxane, dimethylpolysiloxane, and mehylphenylpolysiloxane; animal or vegetable fats and oils, such as squalane and palm oil; hydrocarbons; higher fatty acid esters; liquid paraffin; liquid isoparaffin; and the like.

The cosmetics of the present invention may contain, if desired, various components employed in common cosmetics in a proportion that will not impair the effects of the present invention. Such components include solid or semi-solid oily components, such as vaseline, lanoline, ceresine, microcrystalline wax, carnauba wax, candelilla wax, higher fatty acids, and higher alcohols; water-soluble or oil-soluble polymers; colorants, such as organic or inorganic pigments, silicone- or fluorine compound-treated organic or inorganic pigments, and organic dyes; surfactants, such as anionic, cationic or nonionic surfactants, dimethylpolysiloxane-polyoxyalkylene copolymers, and polyether-modified silicones; water; antiseptics, antioxidants, dyestuffs, thickeners, pH adjusting agents, perfumes, ultraviolet absorbents, humectants, blood flow accelerators, agents for giving a cool feel, anhidrotics, bactericides, and skin activators. Addition of fluorine compound-treated pigments is recommended for preventing makeup from getting disordered due to sebum.

The cosmetics of the present invention are not restricted in form or kind and are prepared in a conventional manner. Forms of cosmetics of the present invention include oily cosmetics, emulsified cosmetics, aqueous cosmetics, lipstick, rouge, foundation, skin cleansers, shampoos, hair dressing preparations, hair tonics, and hair growing promoters.

The silicone derivatives (A) of the present invention exhibit excellent characteristics, such as (i) high water-and oil-repellency, (ii) satisfactory compatibility with cosmetic bases, (iii) high emulsion stability, (iv) low viscosity (non-stickiness), (v) high affinity to the skin (hardly come away from the skin), and (vi) extremely low irritation to the skin. Therefore, cosmetics containing silicone derivative (A) wear long and give a good feel on use.

The present invention will now be illustrated in greater detail with reference to examples, but it should be understood that the present invention is not construed as being limited thereto. All the percents are given by weight unless otherwise indicated.

In what follows, the following symbols are used for representing various siloxane units.

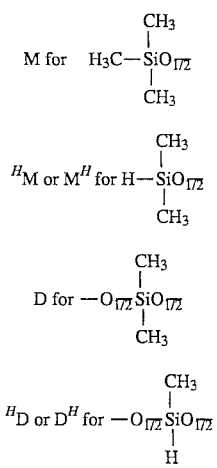

EXAMPLE 1

Preparation of Fluorine-Modified Silicone (1a):

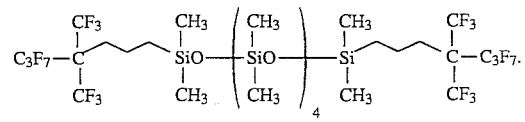

In a 100 ml four-necked flask equipped with a stirrer, a refluxing condenser, and a thermometer were charged 12.0 g (27.8 mmol) of methylhydrogenpolysiloxane ($^{H}MD_4M^{H}$) and 24.1 g (66.8 mmol) of $H_2C\!=\!CHCH_2C(CF_3)_2(C_3F_7)$ (hereinafter referred to as compound (4a)) in a nitrogen atmosphere. After the inner temperature was raised to 80° C., 110.2 μof a 2% isopropyl alcohol solution of chloroplatinic acid ($3.3\times10^{-3}$ mmol) was added to the mixture, followed by stirring for 5 hours. The reaction mixture was cooled to room temperature, and 50 ml of hexane and 1.1 g of activated carbon were added thereto, followed by stirring at room temperature for 1 hour. The activated carbon was separated by filtration, and the solvent was removed by evaporation. The unreacted compound (4a) was removed by distillation under reduced pressure to obtain 30.3 g of the titled compound (1a) as a colorless transparent oily substance (yield: 95%).

$^1$H-NMR ($CDCl_3$; standard: $CHCl_3$ (7.24 ppm)) δ ppm: 0.00–0.05 (m, 36H, —$SiCH_3$), 0.48–0.56 (m, 4H, a*), 1.53–1.61 (m, 4H, b*), 2.08–2.19 (m, 4H, c*)

* Ha, Hb, and Hc are protons at positions shown below.

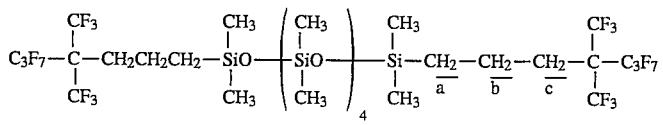

EXAMPLE 2

Preparation of Fluorine-Modified Silicone (1b):

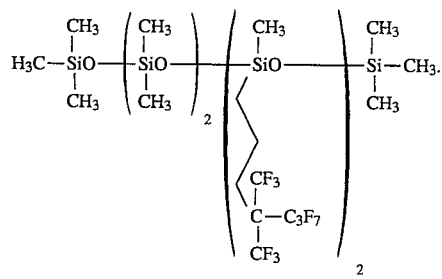

In the same reactor as used in Example 1 were charged 25.0 g (58.0 mmol) of methylhydrogenpolysiloxane ($MD_2D^H{}_2M$) and 50.1 g (139.2 mmol) of compound (4a). After raising the inner temperature to 80° C., 230.0 μl of a 2% isopropyl alcohol solution of chloroplatinic acid (7.0× $10^{-3}$ mmol) was added thereto, and the mixture was stirred for 5 hours. The reaction mixture was worked up in the same manner as in Example 1 to obtain 58.3 g (yield: 87%) of the titled compound (1b) as a colorless transparent oily substance.

$^1$H-NMR (CDCl$_3$; standard: CHCl$_3$ (7.24 ppm)) δ ppm: −0.01–0.06 (m, 36H, —SiCH$_3$), 0.45–0.54 (m, 4H, a*), 1.50–1.73 (m, 4H, b*), 2.09–2.22 (m, 4H, c*)

* Ha, Hb, and Hc are protons at positions shown below.

EXAMPLE 3

Preparation of Fluorine-Modified Silicone (1c):

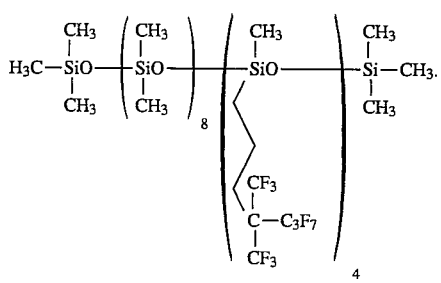

In the same reactor as used in Example 1 were charged 20.0 g (20.1 mmol) of methylhydrogenpolysiloxane ($MD_8D^H{}_4M$) and 34.7 g (96.6 mmol) of compound (4a). After raising the inner temperature to 80° C., 470 μl of a 2% isopropyl alcohol solution of chloroplatinic acid (14.5×$10^{-3}$ mmol) was added thereto, and the mixture was stirred for 5 hours. The reaction mixture was worked up in the same manner as in Example 1 to obtain 45.7 g (yield: 93%) of the titled compound (1c) as a colorless transparent oily substance.

$^1$H-NMR (CDCl$_3$; standard: CHCl$_3$ (7.24 ppm)) δ ppm: 0.00–0.03 (m, 78H, —SiCH$_3$), 0.44–0.53 (m, 8H, a*), 1.50–1.66 (m, 8H, b*), 2.08–2.14 (m, 8H, c*)

* Ha, Hb, and Hc are protons at positions shown below.

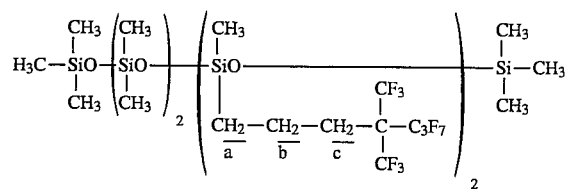

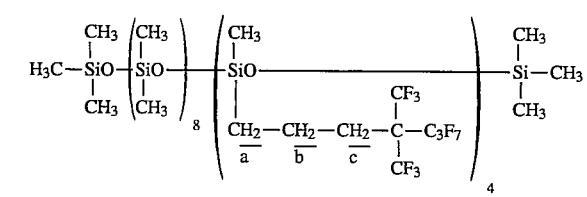

EXAMPLE 4

Preparation of Fluorine-Modified Silicone (1d):

$$H_3C-\underset{\underset{CH_3}{|}}{\overset{\overset{CH_3}{|}}{Si}}O\left(\underset{\underset{CH_3}{|}}{\overset{\overset{CH_3}{|}}{Si}}O\right)_{12}\left(\underset{\underset{\underset{\underset{CF_3}{|}}{\overset{C-C_3F_7}{|}}}{\overset{\overset{CF_3}{|}}{\underset{|}{}}}}{\overset{\overset{CH_3}{|}}{Si}}O\right)_4 \underset{\underset{CH_3}{|}}{\overset{\overset{CH_3}{|}}{Si}}-CH_3.$$

In the same reactor as used in Example 1 were charged 29.5 g (22.8 mmol) of methylhydrogenpolysiloxane $(MD_{12}D^H{}_4M)$ and 39.4 g (109.5 mmol) of compound (4a). After raising the inner temperature to 80° C., 181 μl of a 2% isopropyl alcohol solution of chloroplatinic acid ($5.5\times10^{-3}$ mmol) was added thereto, and the mixture was stirred for 5 hours. The reaction mixture was worked up in the same manner as in Example 1 to obtain 56.0 g (yield: 90%) of the titled compound (1d) as a colorless transparent oily substance.

$^1$H-NMR (CDCl$_3$; standard: CHCl$_3$ (7.24 ppm)) δ ppm: −0.01–0.02 (m, 102H, —SiCH$_3$), 0.44–0.54 (m, 8H, a*), 1.51–1.68 (m, 8H, b*), 2.08–2.15 (m, 8H, c*)

* Ha, Hb, and Hc are protons at positions shown below.

$$H_3C-\underset{\underset{CH_3}{|}}{\overset{\overset{CH_3}{|}}{Si}}O\left(\underset{\underset{CH_3}{|}}{\overset{\overset{CH_3}{|}}{Si}}O\right)_{12}\left(\underset{\underset{\underset{a}{CH_2}-\underset{b}{CH_2}-\underset{c}{CH_2}-\underset{\underset{CF_3}{|}}{\overset{\overset{CF_3}{|}}{C}}-C_3F_7}{\overset{\overset{CH_3}{|}}{Si}O}}{}\right)_4 \underset{\underset{CH_3}{|}}{\overset{\overset{CH_3}{|}}{Si}}-CH_3$$

TEST EXAMPLE 1

The fluorine-modified silicones (1a), (1b), and (1c) prepared in Examples 1 to 3 and comparative compounds hereinafter described (Comparative Examples 1 to 3) were evaluated in terms of water- and oil-repellency, compatibility with silicone, and retention on the skin according to the following test methods and standards. The results obtained are shown in Table 1.

(1) Water Repellency:

Samples having a contact angle with water (an angle formed by a film of a sample compound and a water drop) of not smaller than 100° were rated "A", and those having a contact angle with water of not smaller than 70° and smaller than 100° were rated "B".

(2) Oil Repellency:

Samples having a contact angle with squalane (an angle formed by a film of a sample compound and a squalane drop) of not smaller than 50° were rated "A", those having that angle of not smaller than 0° and smaller than 50° were rated "B", and those having that angle of smaller than 0° were rated "C".

(3) Compatibility with Silicone:

Solubility in octamethylcyclotetrasiloxane was evaluated by examining as to whether 1 g of the sample dissolves in 2 g of octamethylcyclotetrasiloxane. Samples soluble in the silicone were rated "A", and those which were incompatible with the silicone, undergoing phase separation, were rated "B".

(4) Retention on the Skin:

One gram of black iron oxide and 1 g of a test compound were uniformly blended. The resulting paste was applied thin to the center of the forehead of a male. After 4 hours, a sheet of tissue was pressed thereto under pressure of 200 gwt/cm$^2$, and the degree of coloring of the tissue with transferred black iron oxide was rated as follows as an indication of the degree of retention of the compound on the skin when formulated into a cosmetic.

A: Hardly colored.

B: Slightly colored.

C: Colored.

D: Considerably colored.

(5) Viscosity:

The viscosity of the sample was measured by means of Ostward's viscometer at 20° C.

TABLE 1

| Example No. | Contact Angle | | Compatibility with Silicone | Viscosity (cPs) | Retention on the Skin |
|---|---|---|---|---|---|
| | Water Repellency (°) | Oil Repellency (°) | | | |
| Example 1 | A | A | A | 18 | A |
| Example 2 | A | A | A | 45 | A |
| Example 3 | A | A | A | 103 | A |
| Comparative Example 1[1] | B | C | A | 96 | D |
| Comparative Example 2[2] | B | A | B | 139 | C |
| Comparative Example 3[3] | B | C | B | 6 | D |

Note:
[1]: Trifluoropropylsilicone X-22-820, produced by Shin-Etsu Chemical Co., Ltd.
[2]: FSL-300, produced by Asahi Glass Co., Ltd.
H$_3$C — CH$_3$CH$_3$SiO —— CH$_3$CH$_3$SiO $\phantom{xx}_r\phantom{xx}$ CH$_3$SC$_4$F$_9$iO
$\phantom{xx}_s$ CH$_3$CH$_3$Si; — CH$_3$
[3]: Dimethylpolysiloxane KF-96A, produced by Shin-Etsu Chemical Co., Ltd.

As is apparent from Table 1, the fluorine-modified silicone derivatives according to the present invention are superior over conventional silicone compounds in repellency to water and oil, have a low viscosity in general, exhibit satisfactory compatibility with a base of cosmetics, and when formulated into a cosmetic preparation, exhibit excellent retention on the skin.

PREPARATION EXAMPLE 1

(Preparation of Fluorine Compound-Treated Sericite)

In a 1 l round-bottom flask (or a kneader) was put 100 g of sericite, and 500 ml of ion-exchanged water was added thereto. To the mixture was added 33 g of an about 17.5% aqueous solution of a perfluoroalkyl phosphate dihydroxyethylamine salt (($C_mF_{m+1}C_2H_4O)_yPO(ONH_2(CH_2CH_2OH))_{3-y}$) (m is from 6 to 18, averaging 9; 1<y<2), followed by stirring at 40° C. The resulting aqueous solution was adjusted to pH 3 or lower by addition of 40 ml of 1N hydrochloric acid thereby to precipitate a perfluoroalkyl phosphate on the surface of the sericite powder. The thus treated sericite powder was collected by filtration, washed with water, and dried to obtain 105 g of fluorine compound-treated sericite.

EXAMPLES 5 TO 7 AND COMPARATIVE EXAMPLES 4 TO 6

(Two-Phase Liquid Foundation)

Two-phase liquid foundation having the composition shown in Table 2 was prepared in the following production method. The resulting two-phase liquid foundation was evaluated in terms of wearability, retention, and feel on the skin in the evaluation method described below. The results are shown in Table 3.

(Production Method)

The oily components (2) to (9), (13) and (14) were dissolved at room temperature, dispersing the pigment component (1) in the oily phase by means of a disper, and adding the aqueous components (10) to (12) with stirring to emulsify, thus the desired two-phase liquid foundation was obtained.

TABLE 2

| Composition (%) | Example 5 | Example 6 | Example 7 | Comparative Example 4 | Comparative Example 5 | Comparative Example 6 |
| --- | --- | --- | --- | --- | --- | --- |
| (1) Fluorine compound-treated pigments (prepared according to Preparation Example 1): | | | | | | |
| Titanium oxide | 6.0 | 6.0 | 6.0 | 6.0 | 6.0 | 6.0 |
| Sericite | 8.0 | 8.0 | 8.0 | 8.0 | 8.0 | 8.0 |
| Iron oxide (red, yellow and black) | 1.2 | 1.2 | 1.2 | 1.2 | 1.2 | 1.2 |
| (2) Octamethylcyclotetrasiloxane | 20.0 | 20.0 | 20.0 | 20.0 | 20.0 | 20.0 |
| (3) Dimethylpolysiloxane-polyoxyalkylene copolymer | 1.0 | 1.0 | 1.0 | 1.0 | 1.0 | 1.0 |
| (4) Fluorine-modified silicone (1a) of Example 1 | 10.0 | — | — | — | — | — |
| (5) Fluorine-modified silicone (1b) of Example 2 | — | 10.0 | — | — | — | — |
| (6) Fluorine-modified silicone (1c) of Example 3 | — | — | 10.0 | — | — | — |
| (7) Dimethylpolysiloxane KF-96A (6 cs) | — | — | — | 10.0 | — | — |
| (8) Fluorine-modified silicone of Comparative Example 1 | — | — | — | — | 10.0 | — |
| (9) Fluorine-modified silicone of Comparative Example 2 | — | — | — | — | — | 10.0 |
| (10) Glycerin | 2.0 | 2.0 | 2.0 | 2.0 | 2.0 | 2.0 |
| (11) Ethanol | 15.0 | 15.0 | 15.0 | 15.0 | 15.0 | 15.0 |
| (12) Water | balance | balance | balance | balance | balance | balance |
| (13) Octyl methoxysuccinate | 2.0 | 2.0 | 2.0 | 2.0 | 2.0 | 2.0 |
| (14) Perfume | trace | trace | trace | trace | trace | trace |

(Evaluation method)

The resulting two-phase liquid foundation was organoleptically evaluated in terms of wearability, retention, and feel on the skin by 10 special panel members based on the following evaluation criterion. In this evaluation, the wearability was evaluated in terms of the degree of a greasy or shiny appearance of the skin 4 hours after application of the foundation. The retention was evaluated in terms of the degree of removal of the foundation from the skin 8 hours after application. The feel on use was evaluated in terms of the general feeling at use including spreadability and suitability and adhesiveness to the skin. The results obtained are shown in Table 3.

A: 8 or more panel members evaluated good.
B: 4 to 7 panel members evaluated good.
C: Less than 4 panel members evaluated good.

TABLE 3

| Example No. | Wearability | Retention | Feel on Use |
| --- | --- | --- | --- |
| Example 5 | A | A | A |
| Example 6 | A | A | A |
| Example 7 | A | A | A |
| Comparative Example 4 | C | C | A |
| Comparative Example 5 | C | C | B |
| Comparative Example 6 | B | B | C |

It is apparent that the liquid foundation according to the present invention is superior in wearability, retention, and feel on use to that containing a conventional silicone compound.

EXAMPLE 8

(Powder Foundation)

A powder foundation of the composition shown in Table 4 below was prepared in the following production method.

(Production method)

Pigment component (1) was pulverized in a grinder and transferred to a high-speed blender. Binder and other components were uniformly mixed by heating, added to the pigment powder, and uniformly mixed. The powder mixture was further ground in a grinder and passed through a sieve to regulate the particle size. After being allowed to stand for a few days, the powder mixture was compression molded into a container, such as a metallic dish, to obtain a powder foundation.

TABLE 4

| Component | Amount (% by weight) |
|---|---|
| (1) Fluorine compound-treated pigments (prepared according to Preparation Example 1): | |
| Titanium oxide | 10.0 |
| Sericite | 30.0 |
| Mica | balance |
| Kaoline | 5.0 |
| Red ion oxide | 0.8 |
| Yellow iron oxide | 2.5 |
| Black iron oxide | 0.1 |
| (2) Fluorine-modified silicone (1a) of Example 1 | 8.0 |
| (3) Bees wax | 2.0 |
| (4) Antiseptic | 0.2 |
| (5) Perfume | trace |

EXAMPLE 9

(Rouge)

Rouge of the composition shown in Table 5 below was prepared in the same manner as in Example 8.

TABLE 5

| Component | Amount (% by weight) |
|---|---|
| (1) Silicone-treated pigments (commercially available methylhydrogenpolysiloxane-treated pigments): | |
| Kaolin | balance |
| Mica | 13.0 |
| Titanium oxide | 12.0 |
| Red No. 202 | 2.5 |
| Iron oxide (red, yellow and black) | 5.0 |
| (2) Fluorine-modified silicone (1b) of Example 2 | 7.0 |
| (3) Dimethylpolysiloxane KF-96A (6 cs) | 5.0 |
| (4) Antiseptic | 0.1 |
| (5) Perfume | trace |

EXAMPLE 10

(Powder Eye Shadow)

Powder eye shadow of the composition shown in Table 6 below was prepared in the following production method.
(Production Method)

Powder eye shadow was obtained in the same manner as in Example 8 except that the pigments other than micaceous titanium were first mixed and ground, and micaceous titanium was then added thereto.

TABLE 6

| Component | Amount (% by weight) |
|---|---|
| (1) Water- and oil-repellent powder (a mixture of fluorine compound-treated pigments separately prepared in the same manner as in Preparation Example 1): | |
| Micaceous titanium | 4.9 |
| Sericite | balance |
| Mica | 25.0 |
| Iron oxide (red, yellow and black) | 2.0 |
| Ultramarine | 9.0 |
| Prussian blue | 12.0 |

TABLE 6-continued

| Component | Amount (% by weight) |
|---|---|
| (2) Fluorine-modified silicone (1c) of Example 3 | 8.0 |
| (3) Squalane | 2.0 |
| (4) Vaseline | 1.5 |
| (5) Sorbitan trioleate | 1.0 |
| (6) Antiseptic | 0.1 |
| (7) Perfume | trace |

EXAMPLE 11

(Powder Foundation (for both wet and dry application))

Powder foundation for both dry and wet application (applicable with either a dry applicator or a water-wet applicator) of the composition shown in Table 7 was prepared in the same manner as in Example 10.

TABLE 7

| Component | Amount (% by weight) |
|---|---|
| (1) Silicone-treated pigments (commercially available methylhydrogenpolysiloxane-treated pigments): | |
| Mica | balance |
| Talc | 4.8 |
| Titanium oxide | 14.0 |
| Micaceous titanium | 3.5 |
| Iron oxide (red, yellow and black) | 8.2 |
| Zinc oxide | 4.5 |
| Aluminum oxide | 10.0 |
| Barium sulfate | 5.0 |
| (2) Fluorine-modified silicone (1a) of Example 1 | 6.0 |
| (3) Lanoline | 3.0 |
| (4) Vaseline | 1.0 |
| (5) Isopropyl myristate | 1.0 |
| (6) Antiseptic | 1.5 |
| (7) Perfume | trace |

EXAMPLE 12

(Two-Phase Type Sun-Screening Emulsion)

A two-phase type sun-screening emulsion of the composition shown in Table 8 was prepared in the same manner as in Examples 5 to 7.

TABLE 8

| Component | Amount (% by weight) |
|---|---|
| (1) Octamethylcyclotetrasiloxane | 25.0 |
| (2) Fluorine-modified silicone (1b) of Example 2 | 15.0 |
| (3) Dimethylpolysiloxane-polyoxyalkylene copolymer | 1.0 |
| (4) Glycerin | 2.0 |
| (5) Ethanol | 12.0 |
| (6) Purified water | balance |
| (7) Octyl methoxysuccinate | 2.0 |
| (8) Silicone-treated pigments (commercially available methylhydrogenpolysiloxane-treated pigments): | |
| Zinc oxide | 5.5 |
| Titanium oxide | 2.0 |
| Talc | 5.0 |

TABLE 8-continued

| Component | Amount (% by weight) |
| --- | --- |
| (9) Perfume | trace |

EXAMPLE 13

(Nourishing Cream)

Nourishing cream of the composition shown in Table 9 was prepared in the following production method.
(Production Method)

Components (1) to (5) were mixed and heated to 75° C. Components (6), (7), and (10) were mixed together and heated to 70° C., and the resulting mixture was added to the above mixture of (1) and (5) while stirring to emulsify. The emulsion was cooled to 60° C., and components (8) and (9) were added thereto, followed by cooling to room temperature to obtain nourishing cream.

TABLE 9

| Component | Amount (% by weight) |
| --- | --- |
| (1) Polyoxyethylene(50) hardened castor oil | 2.0 |
| (2) Potassium sulfate | 0.5 |
| (3) Fluorine-modified silicone (1c) of Example 3 | 6.0 |
| (4) Liquid paraffin | 5.0 |
| (5) Hexadecyl 2-ethylhexanoate | 2.0 |
| (6) Sodium benzoate | 0.3 |
| (7) Propylene glycol | 2.0 |
| (8) dl-α-Tocopherol acetate | 0.1 |
| (9) Perfume | 0.1 |
| (10) Purified water | balance |

EXAMPLE 14

(Hand Cream)

Hand cream of the composition shown in Table 10 was prepared in the following production method.
(Production Method)

Components (1) to (5) were mixed and heated to 75° C. To the mixture was added slowly a mixture of components (6) to (8) with stirring to emulsify. The emulsion was cooled to room temperature to obtain hand cream.

TABLE 10

| Component | Amount (% by weight) |
| --- | --- |
| (1) Polyoxyethylene(20) sorbitan palmitate | 1.5 |
| (2) Aluminum chloride | 0.8 |
| (3) Isopropyl myristate | 4.5 |
| (4) Dimethylpolysiloxane KF-96A (6 cs) | 4.0 |
| (5) Fluorine-modified silicone (1a) of Example 1 | 6.0 |
| (6) Methyl para-hydroxybenzoate | 0.2 |
| (7) Sorbitol | 10.0 |
| (8) Purified water | balance |

EXAMPLE 15

(Creamy Foundation (W/O Emulsion))

Creamy foundation of the composition shown in Table 11 was prepared in the following production method.
(Production Method)

Components (1) to (6) were mixed and heated to 75° C. Component (7) was dispersed therein by means of a disper. To the mixture was added slowly a mixture of components (9) to (14), heated to 75° C., while stirring to emulsify. After cooling the emulsion to 30° C., components (8) and (15) were added thereto, followed by cooling to room temperature to obtain W/O type creamy foundation.

TABLE 11

| Component | Amount (% by weight) |
| --- | --- |
| (1) Dimethylpolysiloxane-polyoxyalkylene copolymer | 2.0 |
| (2) Fluorine-modified silicone (1b) of Example 2 | 10.0 |
| (3) Dimethylpolysiloxane KF-96A (6 cs) | 5.0 |
| (4) Aluminum stearate | 0.2 |
| (5) 1-Isostearoyl-3-myristoyl glycerol | 2.0 |
| (6) Octyl methoxysuccinate | 2.0 |
| (7) Fluorine compound-treated pigments (prepared in the same manner as in Preparation Example 1): | |
| Talc | 5.0 |
| Titanium oxide | 9.0 |
| Iron oxide (red, yellow and black) | 1.2 |
| (8) Decamethylcyclopentasiloxane | 15.0 |
| (9) Butyl para-hydroxybenzoate | 0.1 |
| (10) Sodium benzoate | 0.2 |
| (11) Magnesium sulfate | 0.5 |
| (12) Glycerin | 5.5 |
| (13) 1,3-Butylene glycol | 2.5 |
| (14) Purified water | balance |
| (15) Perfume | 0.1 |

EXAMPLE 16

(Disinfectant Cream)

Disinfectant cream of the composition shown in Table 12 was prepared in the following production method.
(Production Method)

Components (6) to (11) were mixed uniformly, and the mixture was emulsified in a mixture of aqueous components (1) to (5) to obtain disinfectant cream.

TABLE 12

| Component | Amount (% by weight) |
| --- | --- |
| (1) Polyoxyethylene(50) hardened castor oil | 0.5 |
| (2) Polyoxyethylene(20) sorbitan palmitate | 1.0 |
| (3) Glycerin | 6.0 |
| (4) 1,3-Butylene glycol | 6.0 |
| (5) Purified water | balance |
| (6) Squalane | 5.0 |
| (7) Jojoba oil | 5.0 |
| (8) Octamethylcyclotetrasiloxane | 18.0 |
| (9) Octyl methoxysuccinate | 2.0 |
| (10) Fluorine-modified silicone (1c) of Example 3 | 30.0 |
| (11) Bactericide Irgasan DP-300 | 0.2 |

All the cosmetics obtained in Examples 5 to 16 wore well when applied to the skin and had an excellent feel.

While the invention has been described in detail and with reference to specific examples thereof, it will be apparent to one skilled in the art that various changes and modifications can be made therein without departing from the spirit and scope thereof.

What is claimed is:

1. A fluorine-modified silicon compound having a polymerization degree of from 1 to 400 and containing at least one siloxane unit represented by formula (1):

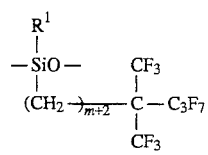

wherein $R^1$ represents an aliphatic straight-chain or branched hydrocarbon group having 1 to 20 carbon atoms, an alicyclic hydrocarbon group having 5 to 10 carbon atoms or an aromatic hydrocarbon group having 6 to 10 carbon atoms; and m represents 0 or an integer of from 1 to 10.

2. The fluorine-modified silicon compound of claim 1, which comprises 1 to 200 siloxane units represented by formula (1) and from 0 to 200 siloxane units represented by formula (2):

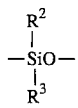

wherein $R^2$ and $R^3$, which may be the same or different, each represent an aliphatic straight-chain or branched hydrocarbon group having 1 to 20 carbon atoms, an alicyclic hydrocarbon group having 5 to 10 carbon atoms or an aromatic hydrocarbon group having 6 to 10 carbon atoms.

3. A process for preparing a fluorine-modified silicon compound having a polymerization degree of from 1 to 400 and containing at least one siloxane unit represented by formula (1):

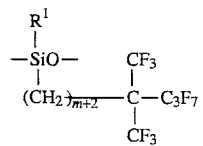

wherein $R^1$ represents an aliphatic straight-chain or branched hydrocarbon group having 1 to 20 carbon atoms an alicyclic hydrocarbon group having 5 to 10 carbon atoms or an aromatic hydrocarbon group having 6 to 10 carbon atoms; and m represents 0 or an integer of from 1 to 10, which comprises reacting a silicon compound having a polymerization degree of from 1 to 400 and containing a siloxane unit represented by formula (3):

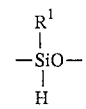

wherein $R^1$ is as defined above, with a perfluoroalkyl compound represented by formula (4):

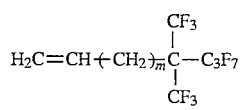

wherein m represents 0 or an integer of from 1 to 10.

4. A cosmetic containing a fluorine-modified silicon compound having a polymerization degree of from 1 to 400 and containing at least one siloxane unit represented by formula (1):

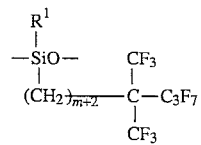

wherein $R^1$ represents an aliphatic straight-chain or branched hydrocarbon group having 1 to 20 carbon atoms an alicyclic hydrocarbon group having 5 to 10 carbon atoms or an aromatic hydrocarbon group having 6 to 10 carbon atoms; and m represents 0 or an integer of from 1 to 10.

* * * * *